United States Patent
Weigl et al.

(10) Patent No.: US 10,005,791 B2
(45) Date of Patent: Jun. 26, 2018

(54) O-DEMETHYLATING PROCESS OF METHOXY SUBSTITUTED MORPHINAN-6-ONE DERIVATIVES

(71) Applicant: CILAG AG, Schaffhausen (CH)

(72) Inventors: Georg Ulrich Weigl, Schaffhausen (CH); Dominik Stefan Stämpfli, Schaffhausen (CH); Nelli Maurer, Schaffhausen (CH)

(73) Assignee: Noramco GmbH, Neuhausen am Rheinfall (CH)

( * ) Notice: Subject to any disclaimer, the term of this patent is extended or adjusted under 35 U.S.C. 154(b) by 0 days. days.

(21) Appl. No.: 15/302,830

(22) PCT Filed: Apr. 7, 2015

(86) PCT No.: PCT/EP2015/057508
§ 371 (c)(1),
(2) Date: Oct. 7, 2016

(87) PCT Pub. No.: WO2015/155181
PCT Pub. Date: Oct. 15, 2015

(65) Prior Publication Data
US 2017/0022211 A1    Jan. 26, 2017

(30) Foreign Application Priority Data

Apr. 10, 2014  (EP) .................................... 14164132
Sep. 30, 2014  (EP) .................................... 14186982

(51) Int. Cl.
*C07D 489/08*    (2006.01)
(52) U.S. Cl.
CPC ................... *C07D 489/08* (2013.01)
(58) Field of Classification Search
None
See application file for complete search history.

(56) References Cited

PUBLICATIONS

Schmidhammer, H. et al. Synthesis and Biological Evaluation of 14-Alkoxymorphinans. 17. Highly Opioid Receptor Selective 14-Alkoxy-Substituted Indolo- and Benzofuromorphinans. J. Med. Chem. 2002, p. 5381.*
Asnawi, A. et al. Demethylation of Quinine Using Anhydrous Aluminum Trichloride. ITB J. Sci. 2011, vol. 43A, p. 44.*
SIGMA Aldrich—Methylene Chloride (accessed Mar. 14, 2017).*
Asnawi, A., et al., "Demethylation of Quinine Using Anhydrous Aluminum Trichloride," ITB Journal of Sciences, Jan. 1, 2011, pp. 43-50, vol. 43, No. 1.
Burwell, R.L., "The Cleavage of Ethers," Chemical Reviews, American Chemical Society, Aug. 1, 1954, pp. 615-685, vol. 54, No. 4.
Lacko, E., et al., "A Novel Opioid Receptor Ligand with High In Vitro and In Vivo Against Efficacy," Current Medicinal Chemistry, Oct. 1, 2012, pp. 4699-4707, vol. 19, No. 27.
Schuetz, J., et al., "Synthesis and Biological Evaluation of 14-Alkoxymorphinans. 17. Highly delta Opioid Receptor Selective 14-Alkoxy-Substituted Indolo- and Benzofuromorphinans," Journal of Medicinal Chemistry, American Chemical Society, Jan. 1, 2002, pp. 5378-5383, vol. 45.
Weiss, U., "Derivatives of Morphine. II. Demethylation of 14-hydroxycodeinone. 14-Hydroxymorphinone and 8,14-Dihydroxymorphinone," The Journal of Organic Chemistry, American Chemical Society, Nov. 1, 1957, pp. 1505-1508, vol. 22, No. 11.
Zhang, A, et al., "Supporting Material: Synthesis of 2-Fluoro-11-hydroxy-N-propylnoraporphine—a potential dopamine D2 agonist," Organic Letters, American Chemical Society, Jun. 18, 2005, pp. 3239-3242.
Zhang, A, et al., "Synthesis of 2-Fluoro-11-hydroxy-N-propylnoraporphine: A Potential Dopamine D2 Agonist," Organic Letters, American Chemical Society, Jul. 21, 2005, pp. 3239-3242, vol. 7, No. 15.
Zheng, Y., et al., "Improvement on the synthetic process of Naloxone," Fudan University Journal of Medical Sciences, Mar. 19, 2007, pp. 888-890, vol. 34, No. 6.
International Search Report and Written Opinion for International Application No. PCT/EP2015/057508 dated Oct. 15, 2015.

* cited by examiner

*Primary Examiner* — Niloofar Rahmani
(74) *Attorney, Agent, or Firm* — Alston & Bird LLP

(57) ABSTRACT

The present invention relates to an improved process for O-demethylating methoxy substituted morphinan-6-one derivatives using AlCl3 as a demethylating agent in a reaction-inert solvent having a water content ranging from 0.1% wt to 0.8% wt. 10.

13 Claims, No Drawings

O-DEMETHYLATING PROCESS OF METHOXY SUBSTITUTED MORPHINAN-6-ONE DERIVATIVES

CROSS-REFERENCE TO RELATED APPLICATIONS

This application is a U.S. National Stage Entry of International Patent Application No. PCT/EP2015/057508, filed 7 Apr. 2015, entitled "O-Demethylating Process of Methoxy Substituted Morphinan-6-One Derivatives", which in turn claims the benefit of EP Priority Patent Application Nos.: EP 14164132.4 filed 10 Apr. 2014 and EP 14186982.6 filed 30 Sep. 2014, each of which is incorporated by reference herein in its entirety.

FIELD OF THE INVENTION

The present invention relates to an improved process for O-demethylating methoxy substituted morphinan-6-one derivatives using $AlCl_3$ as a demethylating agent in a reaction-inert solvent having a water content ranging from about 0.1% wt to about 0.8% wt.

BACKGROUND OF THE INVENTION

The morphinan compounds are a group of structurally related alkaloids that can act as opiate receptor agonists or opiate receptor antagonists. Opiate receptor agonists such as e.g. morphine, codeine, hydrocodone, oxycodone, hydromorphone, oxymorphone, and nalbuphine, are of use as analgesics for pain relief. Compounds such as nalmefene, naltrexone and naloxone are opiate receptor antagonists useful for the treatment of substance abuse or to reverse the effects of opiate agonists.

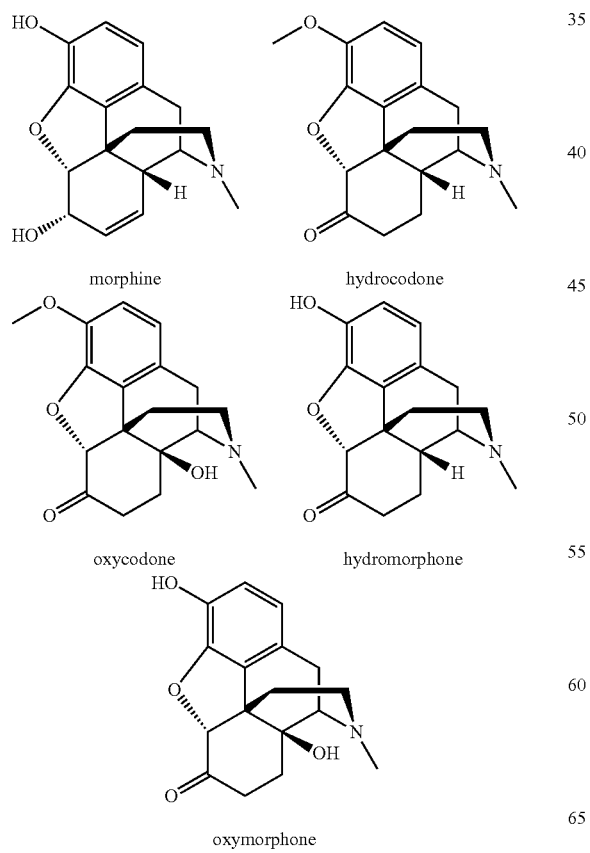

morphine hydrocodone oxycodone hydromorphone oxymorphone

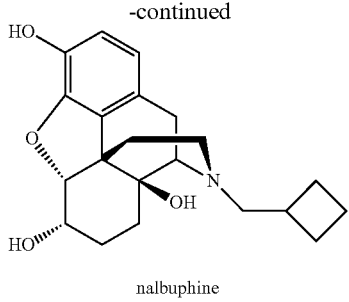

nalbuphine

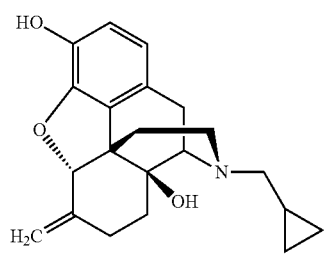

nalmefene

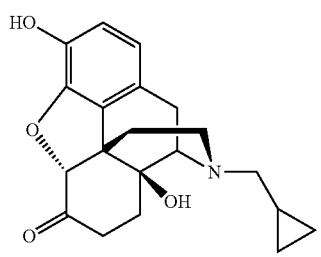

naltrexone

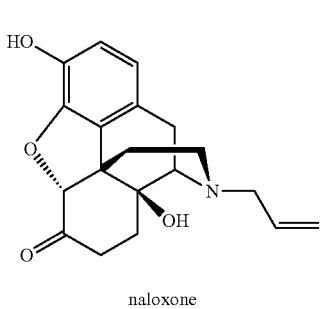

naloxone

A process for preparing 14-hydroxymorphinone by O-demethylating 14-hydroxy-codeinone is described by Ulrich Weiss in Journal of Organic Chemistry, p. 1505-1508 (1957), by brief treatment of 14-hydroxycodeinone with a concentrated aqueous solution of hydrobromic acid at 120° C., removal of non-phenolic material by extraction with chloroform from alkaline medium, and extraction of the phenolic reaction products with chloroform or chloroform-ethanol at pH=8-9. The reported yields are modest and variable ranging between 35% and 52%. Also undesired hydration of the double bond in 14-hydroxymorphinone was also observed.

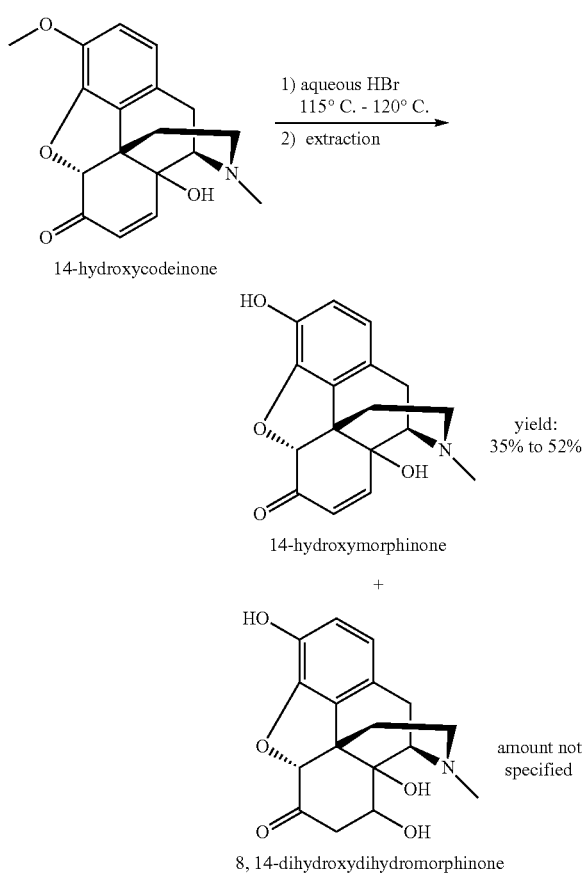

14-hydroxycodeinone 14-hydroxymorphinone
yield: 35% to 52%

+

8,14-dihydroxydihydromorphinone
amount not specified

Hence there is a need for a more efficient process with a higher yield and little or no formation of the undesired 8,14-dihydroxydihydromorphinone.

Another process for process for preparing 14-hydroxymorphinone by O-demethylating 14-hydroxy-codeinone is described by Zhang A. et al. in Organic Letters, vol. 7, no. 15, 3239-3242 (2005) by treatment of 14-hydroxycodeinone with BBr$_3$ in anhydrous dichloromethane. According to the Supporting Material of the Zhang paper 14-hydroxymorphinone was obtained as a pure white solid with a 70% yield. A feasibility study was done to confirm the yield of said described procedure and to check the quality of the obtained material. The procedure in the Zhang paper could not be reproduced successfully. It was found that full conversion to 14-hydroxymorphinone could not be found even after elongated stirring up to 4 days and chromatographic analysis showed large amounts of different byproducts. Following the reported quench procedure and subsequent extraction procedure in accordance with the Zhang paper, the yield was only 15-25% crude product with 70-85% purity that contained up to 10% unreacted 14-hydroxycodeinone. LC-MS analysis of the reaction mixture showed that during the aqueous work-up procedure HBr was formed when unreacted BBr$_3$ was hydrolysed resulting in a side reaction of HBr addition to the double bond.

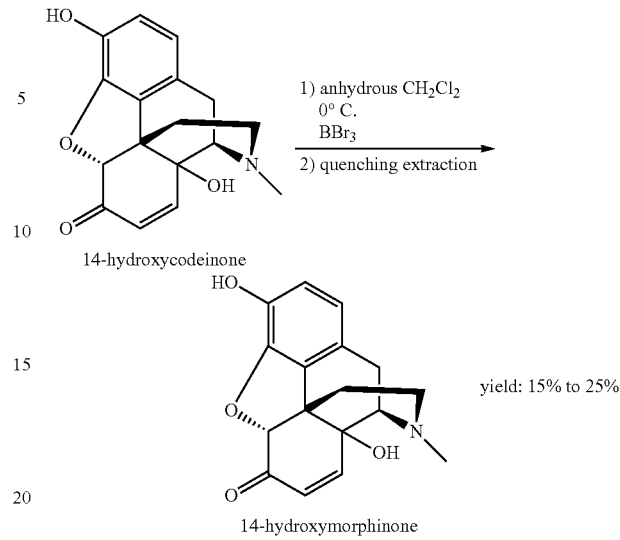

14-hydroxycodeinone 14-hydroxymorphinone
yield: 15% to 25%

Better results were achieved by quenching the reaction mixture into an aqueous borate buffer solution at pH 8.5 to 9.0, which was held in the appropriate pH-range by addition of an aqueous ammonia solution. This procedure delivered crude yields of 72% to 81%, however also under these conditions purities were only between 75% and 85% and still 3.5% to 11% unreacted 14-hydroxycodeinone was present in the end-product.

Hence there is a need for a more efficient process with a higher yield whereby little or no unreacted starting material is found after work-up procedures. Additionally the use of the highly corrosive BBr$_3$, which releases HBr fumes very easily upon contact with water, should be avoided.

The use of AlCl$_3$ as a demethylation agent is described by Asnawi A. et al. in ITB J. Sci., vol. 43a, no. 1, 43-50 (2011) and by Burwell R. L. in Chem. Rev., 615-685 (1954).

It has now been found that O-demethylation of methoxy substituted morphinan-6-one derivatives of formula (II), e.g. 14-hydroxycodeinone, can be performed with a higher yield, higher purity, and little or no undesired hydration of the double bond, using AlCl$_3$ as the demethylating agent in a reaction-inert solvent having a water content ranging from 0.1% wt to 0.8% wt.

DESCRIPTION OF THE INVENTION

In one aspect, the present invention relates to a process for preparing a compound of formula (I), which is characterized by the steps of O-demethylating a compound of formula (II) in a reaction-inert solvent having a water content ranging from 0.1% wt to 0.8% wt using a demethylating agent wherein said demethylating agent is AlCl$_3$,

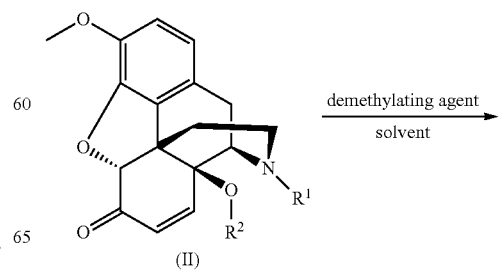

(II)

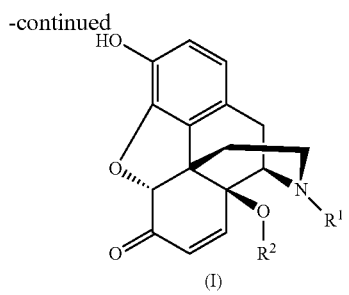

(I)

wherein
$R^1$ is hydrogen, $C_{1-6}$alkyl, $C_{2-6}$alkenyl, or $CH_2$ substituted with $C_{3-6}$cycloalkyl; and
$R^2$ is hydrogen, $C_{1-4}$alkyl, $C_{1-4}$alkylcarbonyl, $C_{1-4}$alkyloxycarbonyl, benzyl, or benzoyl.

As used in the foregoing definitions:
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;
$C_{1-6}$alkyl is meant to include $C_{1-4}$alkyl and the higher homologues thereof having 5 or 6 carbon atoms, such as, for example, 2-methylbutyl, pentyl, hexyl and the like;
$C_{3-6}$cycloalkyl is generic to cyclopropyl, cyclobutyl, cyclopentyl and cyclohexyl;
$C_{2-6}$alkenyl defines straight and branched chain unsaturated hydrocarbon radicals having from 2 to 6 carbon atoms, such as ethenyl, propenyl, butenyl, pentenyl or hexenyl.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that where a range is recited, the range is not limited to the recited upper and lower bounds, but rather includes the full range from about amount X through about amount Y, or any amount or range therein.

Interesting processes of the present invention are those wherein one or more of the following restrictions apply to the compounds of formula (II):
a) $R^1$ is hydrogen; or
b) $R^1$ is $C_{1-4}$alkyl; or
c) $R^1$ is methyl; or
d) $R^2$ is hydrogen; or
e) $R^1$ is methyl and $R^2$ is hydrogen; or
f) $R^1$ is hydrogen and $R^2$ is hydrogen; or
g) $R^1$ is $CH_2$-cyclopropyl and $R^2$ is hydrogen; or
h) $R^1$ is —$CH_2$—CH=$CH_2$ and $R^2$ is hydrogen.

The reaction-inert solvent can be any solvent such as e.g. toluene, fluorobenzene, trifluorotoluene, chlorobenzene, 1,2-dichlorobenzene, 1,3-dichlorobenzene, 1,4-dichlorobenzene, 1,2,4-trichloro-benzene, benzene, tetrachloromethane, trichloromethane, dichloromethane, nitrobenzene, 1-chloro-2-nitrobenzene, 1-chloro-3-nitrobenzene, 1-chloro-4-nitrobenzene, tetraalkylammonium chloride, tetraalkylammonium bromide, or a mixture thereof. In an embodiment the reaction-inert solvent is preferably nitrobenzene.

It has been found that the presence of a small amount of water in the reaction-inert solvent reduces the formation of chlorinated side-products. In practice the reaction-inert solvent comprises an amount of water ranging from about 0.1% wt to about 0.8% wt.

When the solvent is nitrobenzene, the amount of water typically ranges from about 0.2% wt to about 0.3% wt.

The process of the present invention can be performed at a temperature between 20° C. and the reflux temperature of the reaction-inert solvent. When nitrobenzene is used as the reaction-inert solvent, the process is performed at a temperature between about 20° C. and about 150° C. In an embodiment the temperature can range between about 60° C. and about 90° C., or between about 70° C. and about 80° C.

The amount of demethylating agent $AlCl_3$ ranges from about 2 mol to about 4 mol with respect to the compound of formula (II). If less $AlCl_3$ is used the reaction takes longer and may not run to completion. If more $AlCl_3$ is used, more side-products are formed. In an embodiment the amount of $AlCl_3$ is preferably about 3.2 mol with respect to the compound of formula (II).

EXPERIMENTAL PART

Example 1: Preparation of Compounds of Formula (I)

A 350 ml 4-neck flask was equipped with an overhead stirrer, thermostat, thermometer and dropping funnel. Under a nitrogen atmosphere $AlCl_3$ (26.8 g, 201 mmol) was added in small portions to nitrobenzene (110.1 g, with a water content of 0.27 wt %) and the resulting mixture was heated up to 50° C. until a clear solution was obtained (50 minutes) and was then allowed to cool to a temperature of 25° C.

14-Hydroxycodeinone (20 g, 62.8 mmol) was slowly added in portions over a period of 30 minutes. The resulting mixture was heated up to 70° C. and stirred until complete (14 hours). The reaction mixture was cooled down to 25° C. over 30 minutes and an aqueous mixture of acetonitrile (10% wt in water, 150 ml) was added, while stirring for a further 60 minutes. The resulting suspension was filtered and the filtration cake was washed with methylisobutylketone.

The crude product was suspended in methanol and heated up to reflux. The mixture was cooled and the solid residue was isolated by filtration at 0° C. and washed with acetone.

The obtained product was suspended in water, titrated with triethylamine to a pH value of 8.8-9.2 at a temperature of 20° C. to 25° C. After filtration the solid product was washed with water and dried in vacuo to obtain 14-hydroxymorphinone with a yield of 72%. HPLC analysis of the isolated 14-hydroxymorphinone was done using the following analytical procedure.

Analytical Method:
Instrument: Agilent 11011200 series HPLC or equivalent
DAD detector or equivalent
Sample solvent: 10 g of H3PO4 (85 wt %) in 1000 g of water
Column: Interchim Uptisphere Strategy RP, 3 μm, 250× 4.6 mm,
Serial No. 1217919 or equivalent
Cycle time: 86 minutes
Run time (Analysis time) 70 minutes
Equilibration time (Post time) 15 minutes Injection volume: 5 µl, with needle wash, wash solution: acetonitrile/water (1/1)
Mobile phases: A: water (HPLC grade)
B: acetonitrile
C: 50 g of $H_3PO_4$ (85 wt %)/1000 g of water
Gradient:

| Time (minutes) | % A  | % B  | % C  |
|----------------|------|------|------|
| 0              | 73.5 | 3.0  | 23.5 |
| 4              | 73.5 | 3.0  | 23.5 |
| 10             | 71.5 | 5.0  | 23.5 |
| 17             | 66.5 | 10.0 | 23.5 |
| 32             | 61.5 | 15.0 | 23.5 |
| 50             | 51.5 | 25.0 | 23.5 |
| 70             | 13.0 | 63.5 | 23.5 |
| 70.1           | 73.5 | 3.0  | 23.5 |
| 85             | 73.5 | 3.0  | 23.5 |

Flow rate: 0.600 ml/minute
Column Temperature: 30° C.
Detection: UV (205 nm)
HPLC purity of obtained 14-hydroxymorphinone: 99.6%
No formation of 8,14-dihydroxydihydromorphinone was observed.

The invention claimed is:
1. A process for preparing compound (I)

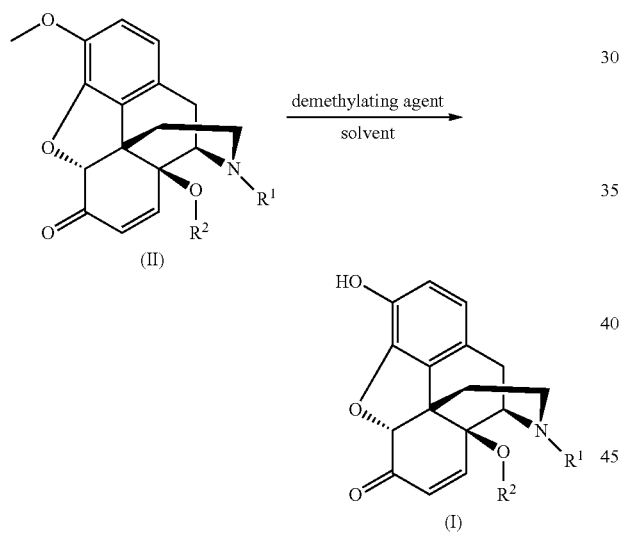

wherein
$R^1$ is hydrogen, $C_{1-6}$ alkyl, $C_{2-6}$ alkenyl, or $CH_2$ substituted with $C_{3-6}$cycloalkyl; and
$R^2$ is hydrogen, $C_{1-4}$alkyl, $C_{1-4}$alkylcarbonyl, $C_{1-4}$alkyloxycarbonyl, benzyl, or benzoyl;
by O-demethylating compound (II) in a reaction-inert solvent having a water content ranging from 0.1% wt to 0.8% wt using a demethylating agent wherein said demethylating agent is $AlCl_3$ present in an amount ranging from 2 to 4 equivalents to compound (II).

2. The process according to claim 1 wherein $R^1$ is hydrogen, —$CH_2$—CH=$CH_2$, $C_{1-4}$alkyl, or $CH_2$-cyclopropyl.

3. The process according to claim 2 wherein $R^1$ is hydrogen.

4. The process according to claim 3 wherein $R^2$ is hydrogen.

5. The process according to claim 2 wherein $R^1$ is $C_{1-4}$alkyl.

6. The process according to claim 5 wherein $R^1$ is methyl.

7. The process according to claim 6 wherein $R^2$ is hydrogen.

8. The process according to claim 1 wherein the reaction-inert solvent is selected from toluene, fluorobenzene, trifluorotoluene, chlorobenzene, 1,2-dichlorobenzene, 1,3-dichlorobenzene, 1,4-dichlorobenzene, 1,2,4-trichlorobenzene, benzene, tetrachloromethane, trichloromethane, dichloromethane, nitrobenzene, 1-chloro-2-nitrobenzene, 1-chloro-3-nitrobenzene, 1-chloro-4-nitrobenzene, tetraalkylammonium chloride, tetraalkylammonium bromide, or a mixture thereof.

9. The process according to claim 8 wherein the reaction-inert solvent is nitrobenzene.

10. The process according to claim 9 wherein the water content of nitrobenzene ranges from 0.2% wt to 0.3% wt.

11. The process according to claim 1 wherein the process is performed at a temperature between 20° C. and the reflux temperature of the solvent.

12. The process according to claim 11 wherein the process is performed at a temperature between 20° C. and 150° C.

13. The process according to claim 1 wherein the demethylating agent $AlCl_3$ is present in an amount of 3.2 equivalents to compound (II).

* * * * *